(12) United States Patent
Baba

(10) Patent No.: US 8,492,166 B2
(45) Date of Patent: Jul. 23, 2013

(54) PARTICLE SUSPENSION AND REAGENT KIT FOR USE IN IMMUNOASSAY

(75) Inventor: Toshiyuki Baba, Wuxi (CN)

(73) Assignee: Sysmex Corporation, Hyogo (JP)

(*) Notice: Subject to any disclaimer, the term of this patent is extended or adjusted under 35 U.S.C. 154(b) by 253 days.

(21) Appl. No.: 12/852,561

(22) Filed: Aug. 9, 2010

(65) Prior Publication Data
US 2011/0053176 A1 Mar. 3, 2011

(30) Foreign Application Priority Data
Aug. 27, 2009 (JP) ................................ 2009-196365

(51) Int. Cl.
*G01N 33/553* (2006.01)
(52) U.S. Cl.
USPC .......................................... 436/525; 436/526
(58) Field of Classification Search
USPC ................................................ 436/525, 526
See application file for complete search history.

(56) References Cited

U.S. PATENT DOCUMENTS

| | | | | |
|---|---|---|---|---|
| 5,629,156 A * | 5/1997 | Shah et al. | ................... | 435/6.11 |
| 2003/0157477 A1* | 8/2003 | Gyuris | .............................. | 435/5 |
| 2004/0101859 A1* | 5/2004 | Moon et al. | ....................... | 435/6 |
| 2007/0172899 A1* | 7/2007 | Graham et al. | .............. | 435/7.21 |

FOREIGN PATENT DOCUMENTS

| | | |
|---|---|---|
| JP | 2006-282582 A | 10/2006 |
| JP | 2007-169209 A | 7/2007 |

* cited by examiner

*Primary Examiner* — Mark Shibuya
*Assistant Examiner* — Pensee Do
(74) *Attorney, Agent, or Firm* — Sughrue Mion, PLLC

(57) ABSTRACT

A particle suspension for use in immunoassay, comprising: particles for use in immunoassay; and a silicone antifoam agent, is disclosed. And a reagent kit for use in immunoassay, comprising: a reagent containing particles and a silicone antifoam agent; another reagent containing an antigen or antibody capable of binding to a target substance and particles; and a further reagent containing a labeled antigen or antibody capable of binding to the target substance, is disclosed.

17 Claims, 8 Drawing Sheets

PARTICLE SUSPENSION AND REAGENT KIT FOR USE IN IMMUNOASSAY

FIELD OF THE INVENTION

The invention relates to a particle suspension for use in immunoassay and to a reagent kit for use in immunoassay.

BACKGROUND

A known immunoassay for detecting an antibody or antigen in a sample is performed using particles on which an antigen or antibody capable of biding to the antibody or antigen to be detected is immobilized. In this method, the particles are brought into contact with the antibody or antigen to be detected so that an antigen-antibody complex is formed on the particles. The antigen-antibody complex formed on the particles is labeled with a marker, which makes it possible to detect the target antibody or antigen.

In general, the above immunoassay is performed using a reagent in which particles having an antigen or antibody immobilized thereon are suspended. In some cases, such suspended particles may aggregate in the reagent. If such a particle aggregate-containing reagent is used in the measurement, the detection accuracy may be reduced. Therefore, particles need to be dispersed sufficiently in the reagent to be used.

It is also known that a certain compound is applied or adsorbed to the surface of particles so that the dispersibility of the particles suspended in a reagent can be improved. For example, Japanese Patent Application Laid-Open (JP-A) No. 2006-282582 discloses a method of coating particle surfaces with citric acid by chemical modification to improve the dispersibility of the particles. JP-A No. 2007-169209 also discloses a method for improving the dispersibility of particles, which includes adsorbing, to the particle surface, a given amount of a dibasic organic acid compound and/or a tribasic organic acid compound. However, the methods disclosed in JP-A Nos. 2006-282582 and 2007-169209 have the problem that the particle surface treatment is complicated and expensive.

SUMMARY OF THE INVENTION

The scope of the present invention is defined solely by the appended claims, and is not affected to any degree by the statements wherein this summary.

A first aspect of the present invention is a particle suspension for use in immunoassay, comprising: particles for use in immunoassay; and a silicone antifoam agent.

A second aspect of the present invention is a reagent kit for use in immunoassay, comprising: a reagent containing particles and a silicone antifoam agent; another reagent containing an antigen or antibody capable of binding to a target substance and particles; and a further reagent containing a labeled antigen or antibody capable of binding to the target substance.

DETAILED DESCRIPTION OF THE PREFERRED EMBODIMENTS

Figure 1:
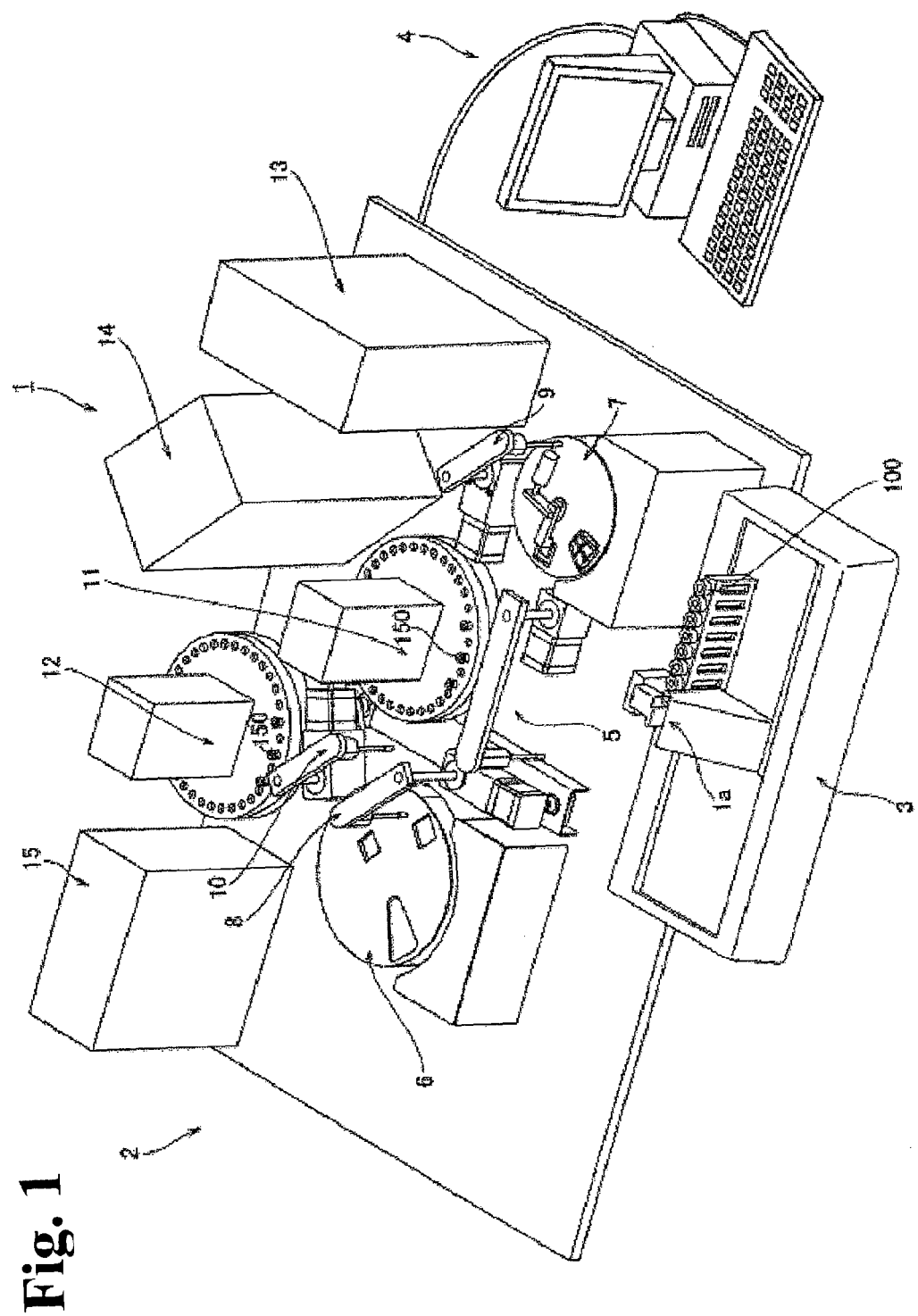
FIG. 1 is a perspective view showing the whole structure of an immunoassay analyzer.

Preferred embodiments of the invention are described below with reference to the drawings.

In an embodiment of the invention, the particle suspension for use in immunoassay contains particles for use in immunoassay and a silicone antifoam agent.

The immunoassay may be of any type as long as it uses particles as a solid phase. In a general immunoassay performed using particles, a target substance as described below is allowed to bind to the particles through an antigen or an antibody, which is capable of binding to the target substance. As a result, a complex containing the target substance and the antigen or antibody is formed on the particles. The complex formed on the particles may be labeled so that the target substance can be detected using the labeling.

The particles may be of any type as long as they are suitable for use in the immunoassay. Examples of particles for use in immunoassay include magnetic particles, latex, red blood cells, and gelatin particles. In an embodiment of the invention, magnetic particles are preferred.

Any type of magnetic particles including a magnetic material as a base material and being suitable for use in the immunoassay may be used. Such magnetic particles are known in the art, examples of which include particles containing $Fe_2O_3$ and/or $Fe_3O_4$, cobalt, nickel, ferrite, or magnetite as a base material.

In an embodiment of the invention, the silicone antifoam agent may be any silicon compound-containing antifoam agent. In an embodiment of the invention, the silicone antifoam agent is preferably a water-soluble silicone antifoam agent in view of use in a water-based system. Specifically, such a water-soluble silicone antifoam agent may be an emulsion type or self-emulsifying silicone antifoam agent. Such a silicone antifoam agent is easily commercially available. Examples of commercially available silicone antifoam agents include KS-538 (Shin-Etsu Chemical Co., Ltd.), KM-70 (Shin-Etsu Chemical Co., Ltd.), KM-72F (Shin-Etsu Chemical Co., Ltd.), TSA 770 (Momentive Performance Materials Inc.), TSA 732 (Momentive Performance Materials Inc.), TSA 7341 (Momentive Performance Materials Inc.), Antifoam SI (Wako Pure Chemical Industries, Ltd.), and SM 5571 (Dow Corning Toray Co., Ltd.). Among these commercially available silicone antifoam agents, Antifoam SI (trade name) is preferred, because it can offer particularly high dispersing performance.

In an embodiment of the invention, the particle suspension may further contain a polycarboxylic acid or a salt thereof. The addition of a polycarboxylic acid or a salt thereof can further increase the dispersibility of the particles in the suspension. Examples of such a polycarboxylic acid or salt thereof include oxalic acid, malonic acid, succinic acid, malic acid, glutaric acid, adipic acid, maleic acid, fumaric acid, tartaric acid, ethylenediamine diacetic acid, iminodiacetic acid, N-(2-acetamido)iminodiacetic acid, tricarballylate, aconitic acid, nitrilotriacetic acid, nitrilotripropionic acid, diaminopropane tetraacetic acid, diaminopropanol tetraacetic acid, and glycol ether diamine tetraacetic acid, or salts thereof. Preferred examples of the polycarboxylic acid or salt thereof include citric acid and tartaric acid or salts thereof. In particular, citric acid or a salt thereof is preferred. More specifically, the polycarboxylic acid or salt thereof may be trisodium citrate dihydrate, potassium sodium tartrate tetrahydrate, or the like.

In an embodiment of the invention, the concentration of a polycarboxylic acid or a salt thereof in the particle suspension for use in immunoassay is not particularly restricted and may be adjusted as needed depending on the dispersibility of the particles in the suspension or the immunoassay conditions. In order to increase the dispersibility of the particles in the suspension, the concentration of a polycarboxylic acid or a salt thereof in the suspension is preferably 0.1 mM or more, particularly preferably 1 mM or more. In order to prevent pH from affecting immunoassay, the concentration of a polycarboxylic acid or a salt thereof in the suspension is preferably 20 mM or less, particularly preferably 10 mM or less. Specifically, the concentration is preferably from 0.1 mM to 20 mM, particularly preferably from 1 mM to 10 mM.

In an embodiment of the invention, the particle suspension for use in immunoassay may further contain any other component which may be added as an agent for immunoassay. Examples of such any other component include a buffer, a preservative, and a serum protein.

In an embodiment of the invention, the reagent kit for use in immunoassay includes a first reagent containing an antigen or antibody capable of binding to a target substance and particles, a second reagent containing the particles and a silicone antifoam agent, and a third reagent containing a labeled antigen or antibody capable of binding to the target substance.

In an embodiment of the invention, the second reagent is the same as the above particle suspension for use in immunoassay.

In an embodiment of the invention, the target substance may be any substance detectable by immunoassay. Specifically, the target substance may be any substance capable of forming, on the particles, a complex containing the target substance and an antigen or an antibody by an antigen-antibody reaction. Examples of the target substance include proteins, nucleic acids, sugars, and lipids. More specifically, examples of the target substance include human immunodeficiency virus (HIV) and antibodies thereto, human T-cell lymphotropic virus type 1 (HTLV-1) and antibodies thereto, hepatitis C virus (HCV) and antibodies thereto, hepatitis B virus (HBV) and antibodies thereto, carcinoembryonic antigen (CEA), C-reactive protein (CRP), PSA, CYFRA, Pro-GRP, *Treponema pallidum* (TP) antibody, CA 19-9, CA 125, CA 15-3, troponin, α1-antitrypsin, α1-microglobulin, β2-microglobulin, TPAb, TgAb, TPOAb, TRAb, haptoglobin, transferrin, ceruloplasmin, ferritin, albumin, hemoglobin A1, hemoglobin A1C, myoglobin, myosin, DUPAN-2, α-fetoprotein (AFP), tissue polypeptide antigen (TPA), brain natriuretic peptide (BNP), apolipoprotein A1, apolipoprotein E, rheumatoid factor, antistreptolysin O (ASO), antithrombin III (AT-III), plasmin-α2-plasmin inhibitor complex (PIC), thrombin-antithrombin III complex (TAT), thrombomodulin (TM), tissue plasminogen activator-plasminogen activator inhibitor I complex (tPAI-C), thyroid hormones (thyroxine (T3), free thyroxine (FT3), triiodothyronine (T4), free triiodothyronine (FT4)), thyroid stimulation hormone (TSH), luteinizing hormone (LH), follicle stimulating hormone (FSH), insulin, SP-A, HCG, prolactin (PRL), E2, progesterone, and so on.

In an embodiment of the invention, the "antigen or antibody capable of binding to the target substance and the particles" in the first reagent may be any antigen or antibody capable of binding to the target substance by an antigen-antibody reaction. The antigen or antibody is also capable of binding to the particles. Any method known in the art may be used to make the antigen or antibody capable of binding to the particles. In a preferred mode, a particle binding site is attached to the antigen or antibody, and a binding substance capable of binding to the particle binding site is immobilized on the particles. This makes it possible to make the antigen or antibody capable of binding to the particles with the aid of the coupling between the particle binding site and the binding substance.

A combination of the particle binding site and the binding substance may be any combination of substances capable of specifically binding to each other under the immunoassay conditions with the reagent kit used in the immunoassay according to an embodiment of the invention. Examples of such a combination include a combination of biotin and any of avidins, a combination of a hapten and an anti-hapten antibody, a combination of nickel and a histidine tag, a combination of glutathione and glutathione-S-transferase, and so on. A combination of the particle binding site and the binding substance is preferably a combination of biotin and any of avidins. Each substance for use in forming a combination of the particle binding site and the binding substance may be used for any one of the particle binding site and the binding substance. In a more preferred combination, the particle binding site may comprise biotin, and the binding substance may comprise any of avidins. As used herein, the term "avidins" is intended to include avidin and streptavidin.

The particle binding site may be attached to the antigen or antibody by any method known in the art. For example, when the particle binding site comprises biotin, the biotin may be attached to an antibody through a group reactive with an amino or thiol group or the like present in antigens or antibodies. The group reactive with an amino group may be a NHS group, and the group reactive with a thiol group may be a maleimide group.

The binding substance may also be immobilized on the particles by any method known in the art. For example, the immobilization may be performed by a physical adsorption method, a covalent bonding method, an ionic bonding method, or any combination thereof. For example, when the binding substance is any of avidins, avidins may be directly immobilized on the particles by physical adsorption. Alternatively, avidins may be immobilized on the particles by coupling avidins to the particles to which a substance capable of binding to avidins, such as biotin, is attached. The method described in JP-A No. 2006-226689 may also be used to immobilize avidins on the particles. Particles to which avidins are attached may also be purchased from JSR Corporation or Dynal Biotech Ltd.

In an embodiment of the invention, the "labeled antigen or antibody capable of binding to the target substance" in the third reagent may be any antigen or antibody that is labeled with a marker and capable of recognizing a binding site of the target substance other than the binding site for the "antigen or antibody capable of binding to the target substance and the particles."

The marker may be any marker usable in general immunoassays. For example, the marker may be an enzyme, a fluorescent substance, a radioisotope, or the like. Examples of the enzyme include alkaline phosphatase, peroxidase, glucose oxidase, tyrosinase, acid phosphatase, and so on. Examples of the fluorescent substance include fluorescein isothiocyanate (FITC), green-fluorescent protein (GFP), luciferin, and so on. Examples of the radioisotope include $^{125}I$, $^{14}C$, $^{32}P$, and so on. In an embodiment of the invention, the marker is preferably an enzyme.

When the marker is an enzyme, the reagent kit preferably further includes a fourth reagent containing a substrate for the enzyme. The substrate to be used may be any substrate known in the art, which may be appropriately selected depending on the enzyme to be used as the marker. For example, when alkaline phosphatase is used as the enzyme, examples of the substrate include a chemiluminescent substrate such as CDP-Star (registered trademark), (disodium 4-chloro-3-(methoxyspiro{1,2-dioxetane-3,2'-(5'-chloro)tricyclo[$3.3.1.1^{3,7}$]decane}-4-yl)phenyl phosphate), CSPD (registered trademark), or (disodium 3-(4-methoxyspiro{1,2-dioxetane-3,2-(5'-chloro)tricyclo[$3.3.1.1^{3,7}$]decane}-4-yl)phenyl phosphate); a luminescent substrate such as p-nitrophenyl phosphate, 5-bromo-4-chloro-3-indolyl phosphate (BCIP), 4-nitro blue tetrazolium chloride (NBT), or iodonitrotetrazolium (INT); a fluorescent substrate such as 4-methylumbelliferyl phosphate (4-MUP); and a chromogenic substrate such as 5-bromo-4-chloro-3-indolyl phosphate (BCIP), disodium 5-bromo-6-chloro-indolyl phosphate, or p-nitrophenyl phosphate.

The antigen or antibody may be labeled with the marker by any method known in the art. For example, the marker may be attached to the antigen or antibody through the thiol group (—SH) of the antigen or antibody by a known method. More specifically, a functional group capable of reacting with the thiol group, such as a maleimide group, may be introduced into the marker, and then the marker may be allowed to react with the antigen or antibody so that the antigen or antibody can be labeled with the marker.

The labeled antigen or antibody may be detected by a known method used in the art, which is selected depending on the type of the marker. For example, when the marker is an enzyme, luminescence, fluorescence or color development generated by the reaction with the substrate may be detected using a spectrophotometer, a luminometer or the like, so that the labeled antigen or antibody can be detected. When the marker is a fluorescent substance, fluorescence from the fluorescent substance may be detected using a spectrophotometer, a luminometer, or the like, so that the labeled antigen or antibody can be detected. When the maker is a radioisotope, radioactive rays from the radioisotope may be detected using a scintillation counter or the like, so that the labeled antigen or antibody can be detected.

In an embodiment of the invention, each reagent contained in the reagent kit for use in immunoassay may be a liquid, or a solid to which water or the like may be added for use.

The liquid reagent may be any solution containing at least above each component dissolved in an appropriate solvent. Such an appropriate solvent may be water or a buffer with a pH of 6 to 10. Examples of the buffer that may be used include phosphate buffered saline (PBS), a triethanolamine hydrochloride buffer (TEA), a Tris-hydrochloric acid buffer (Tris-HCl), 2-morpholine ethanesulfonic acid (MS), and so on. The buffer may contain a known additive such as a surfactant, a preservative solution, or a serum protein.

The solid reagent may be obtained by removing the appropriate solvent from the solution of the component by freeze drying or the like.

In an embodiment of the invention, the reagent kit for use in immunoassay is preferably used in an immunoassay analyzer. A description is given below of a process of measuring an antigen as a measurement object (target substance) in a sample such as blood by means of an immunoassay analyzer 1 in which an immunoassay reagent kit 1000 according to an embodiment of the invention is used.

The reagent kit 1000 for use in immunoassay includes a first reagent containing a trapping antibody capable of binding to a target substance and magnetic particles, a second reagent containing the magnetic particles and a silicone antifoam agent, a third reagent containing a labeled antibody capable of binding to the target substance, and a fourth reagent containing a luminescent substrate.

Figure 2:
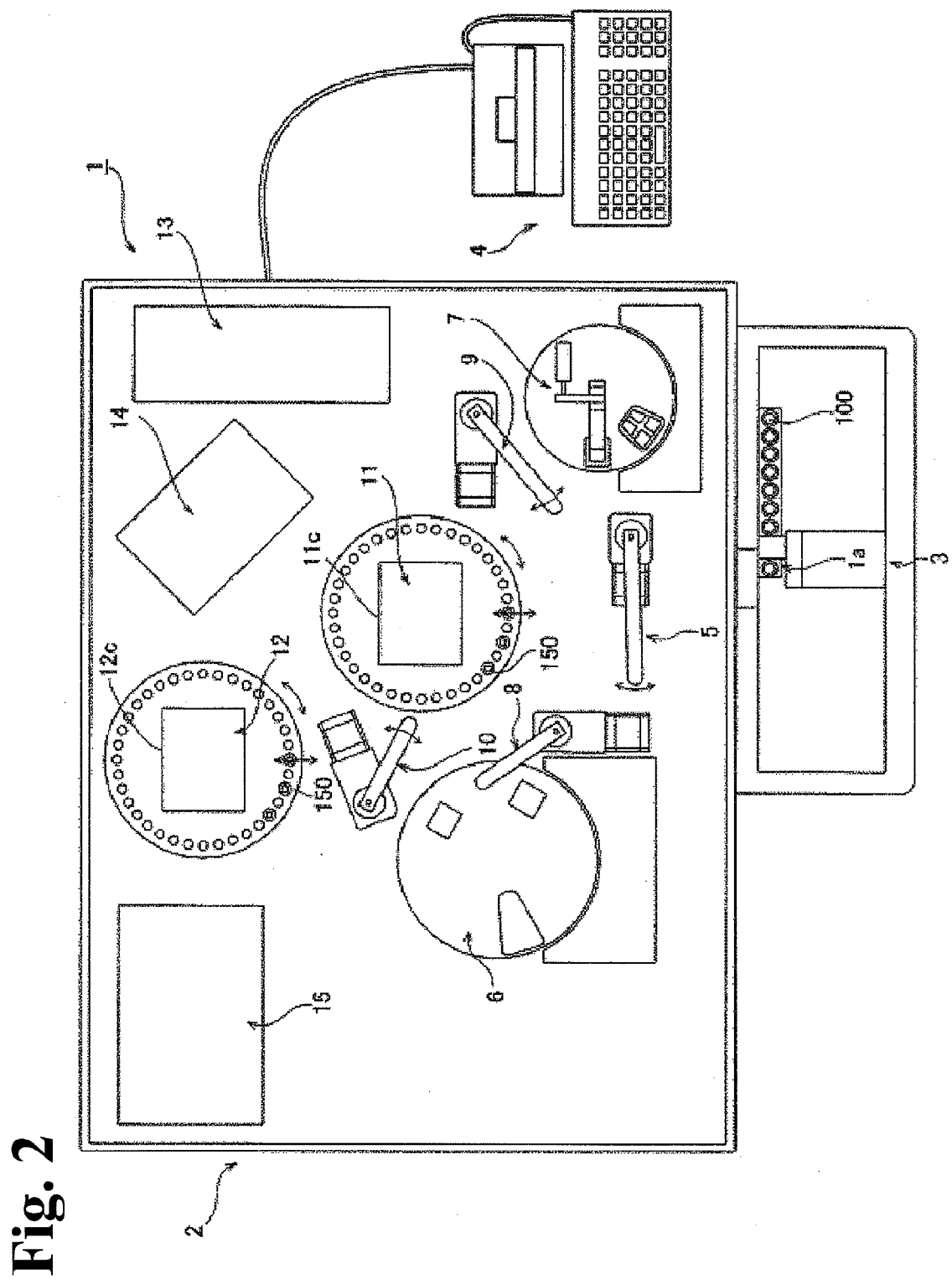
FIG. 2 is a plan view of the immunoassay analyzer shown in FIG. 1.

As shown in FIGS. 1 and 2, the immunoassay analyzer 1 includes a measurement mechanism unit 2, a sample transport unit (sampler) 3 placed on the front side of the measurement mechanism unit 2, and a controller 4 including a PC (personal computer) electrically connected to the measurement mechanism unit 2. The measurement mechanism unit 2 includes a sample pipetting arm 5, reagent holding units 6 and 7, reagent pipetting arms 8, 9 and 10, primary and secondary reaction units 11 and 12, a cuvette supply unit 13, a BF separation unit 14, and a detection unit 15.

First, a sample in a test tube 100 transported to a suction position 1a by the sample transport unit 3 is pipetted, by the sample pipetting arm 5, into a cuvette 150 held in the primary reaction unit 11. The first reagent is then pipetted by the reagent pipetting arm 8 from the reagent holding unit 6 into the cuvette 150 containing the sample and held in the primary reaction unit 11. Thus, the target substance in the sample and the trapping antibody bind together to form a first complex, which contains the target substance and the trapping antibody. The second reagent is then pipetted by the reagent pipetting arm 9 from the reagent holding unit 7 into the cuvette 150 containing the first complex and held in the primary reaction unit 11. Thus, the first complex and the magnetic particles bind together to form a second complex, which contains the first complex and the magnetic particles.

The cuvette 150 is then transported to the BF separation unit 14 by the vessel transport part 11c of the primary reaction unit 11. The BF separation unit 14 then separates the unreacted trapping antibody from the second complex of the sample in the cuvette 150. The cuvette 150 treated by the BF separation unit 14 is then transported to the secondary reaction unit 12 by the vessel transport part 12c of the secondary reaction unit 12. The third reagent is pipetted by the reagent pipetting arm 9 from the reagent holding unit 7 into the cuvette 150 containing the second complex and held in the secondary reaction unit 12. Thus, the second complex and the labeled antibody bind together to form a third complex, which contains the second complex and the labeled antibody. The cuvette 150 is then transported to the BF separation unit 14 by the vessel transport part 12c. The BF separation unit 14 then separates the unreacted labeled antibody from the third complex of the sample in the cuvette 150. The cuvette 150 treated by the BF separation unit 14 is then transported to the secondary reaction unit 12 by the vessel transport part 12c. The fourth reagent is then pipetted by a fourth reagent pipetting arm (not shown) into the cuvette 150 containing the third complex and held in the secondary reaction unit 12. As a result, the labeled antibody of the third complex reacts with the luminescent substrate to generate light. The light is captured by a photo multiplier tube in the detection unit 15, so that the amount of the antigen in the sample is measured.

Figure 3:
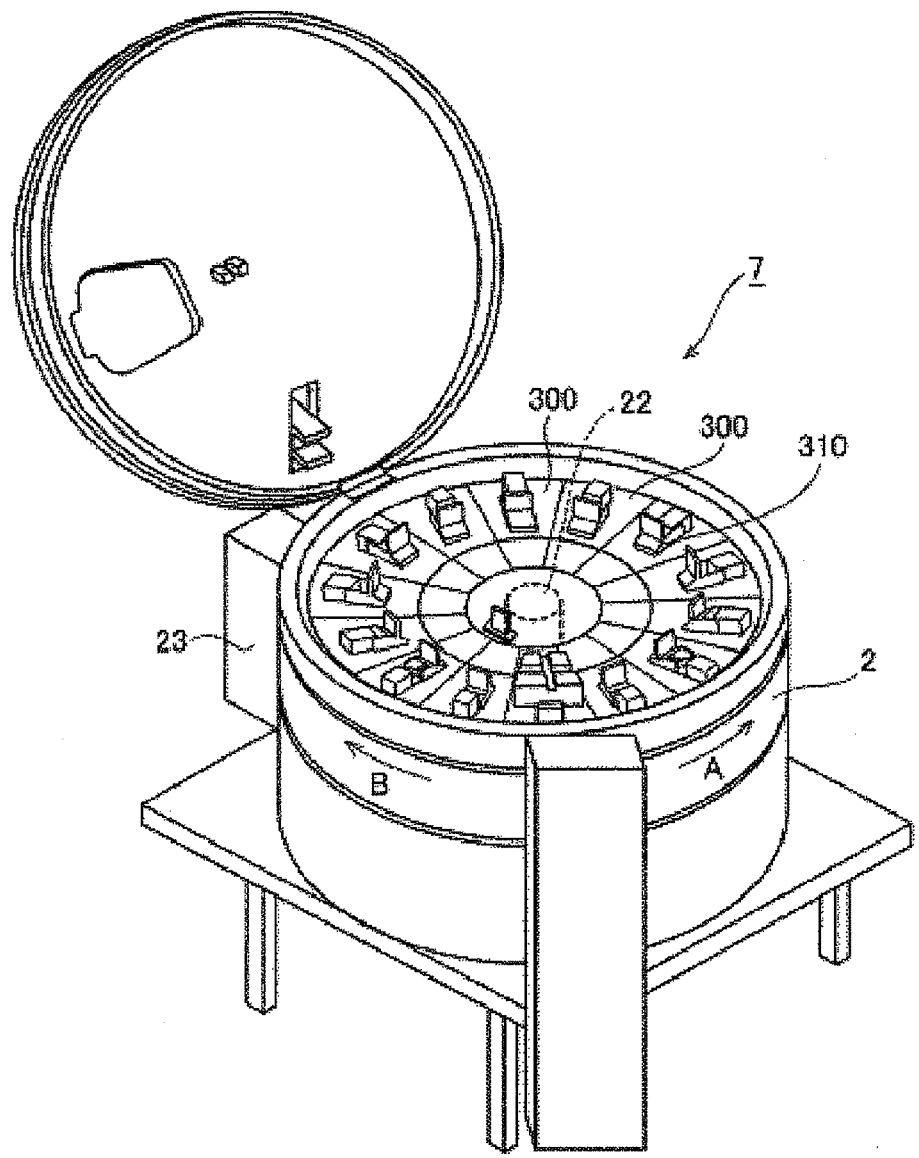
FIG. 3 is a perspective view showing the whole structure of a reagent holding unit shown in FIG. 1.
Figure 4:
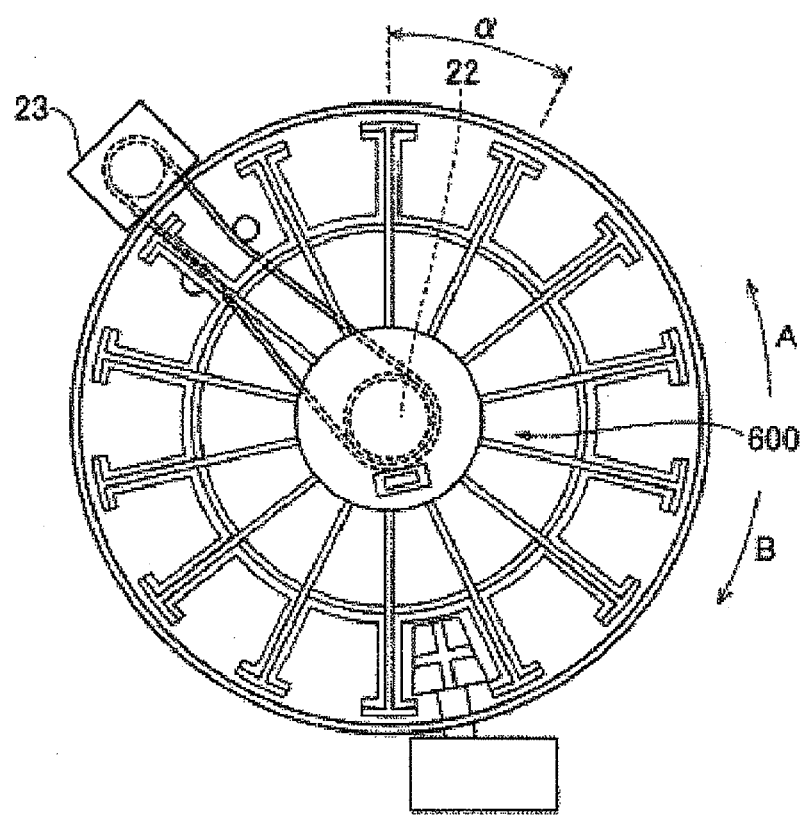
FIG. 4 is a plan view of the reagent storing part of the reagent holding unit shown in FIG. 3.

As shown in FIG. 3, the reagent holding unit 7 is configured to accommodate a reagent storing instrument 300 for holding a reagent vessel 310 containing the second reagent. In this unit, as shown in FIG. 4, the reagent vessel 310 (reagent storing instrument 300) containing the second reagent is held by a rack 600, which is configured so that the rotary shaft 22 can be reciprocally rotated in the arrow directions A and B by the drive of a stepping motor 23. Therefore, the second reagent is agitated by the reciprocal rotation of the rack 600 in the arrow directions A and B so that the magnetic particles, which are heavier than general particles, can be prevented from precipitating. More specifically, the rack 600 is reciprocally rotated at a constant speed through a constant angle α. It will be understood that increasing the speed and the angle α results in sufficient agitation of the reagent. However, the magnetic particles in the second reagent of the reagent kit 1000 according to an embodiment of the invention can be fully dispersed even when each speed is lower than the conventional one, because the second reagent contains a silicone antifoam agent.

Example 1

Preparation of Suspensions 1 to 3 and Buffer for Storing Magnetic Particles
Suspensions 1 to 3 and a buffer for storing magnetic particles were prepared as shown below.
(1) Suspension 1
Commercial magnetic particles (2 μm in average particle size) 0.5%
MES (2-morpholonoethanesulphonic acid) (pH6.5) 20 mM
BSA 0.1%
NaN3 0.1%
(2) Suspension 2
Commercial magnetic particles (2 μm in average particle size) 0.5%
MES (2-morpholonoethanesulphonic acid) (pH6.5) 20 mM
BSA 0.1%
NaN3 0.1%
Antifoam SI (Wako Pure Pure Chemical Industries, Ltd.) 0.015%
(3) Suspension 3
Commercial magnetic particles (2 μm in average particle size) 0.5%
MES (2-morpholonoethanesulphonic acid) (pH6.5) 20 mM
BSA 0.1%
NaN3 0.1%
Antifoam SI (Wako Pure Pure Chemical Industries, Ltd.) 0.015%
Sodium citrate 10 mM
(4) Buffer for Storing Magnetic Particles
MES (2-morpholonoethanesulphonic acid) (pH6.5) 20 mM
BSA 0.1%
NaN3 0.1%

Evaluation of Particle Dispersibility
Four mL of each of Suspensions 1 to 3 was pipetted into the corresponding vessel, fully agitated and allowed to stand. Thereafter, each vessel, in which the magnetic particles were precipitated, was placed in HISCL-2000i (SYSMEX CORPORATION). Agitation operation was then started in HISLC-2000i, and 2 minutes, 4 minutes, 6 minutes, and 10 minutes after the start of the operation, 20 μL of the supernatant of each of Suspensions 1 to 3 was sampled. After the sample was diluted with 980 μL of the buffer for storing magnetic particles, the absorbance of the diluted sample was measured at 600 nm using a spectrophotometer.
The absorbance obtained when the magnetic particles were completely dispersed was normalized as 100%, and the relative absorbance (%) was calculated from the formula below for the evaluation of the dispersibility.

$$\text{Relative absorbance (\%)} = \frac{\text{Absorbance of sample after agitation for } x \text{ minutes}}{\text{Absorbance obtained when the magnetic particles are completely dispersed}} \times 100 \quad \text{Formula (1)}$$

Figure 5:
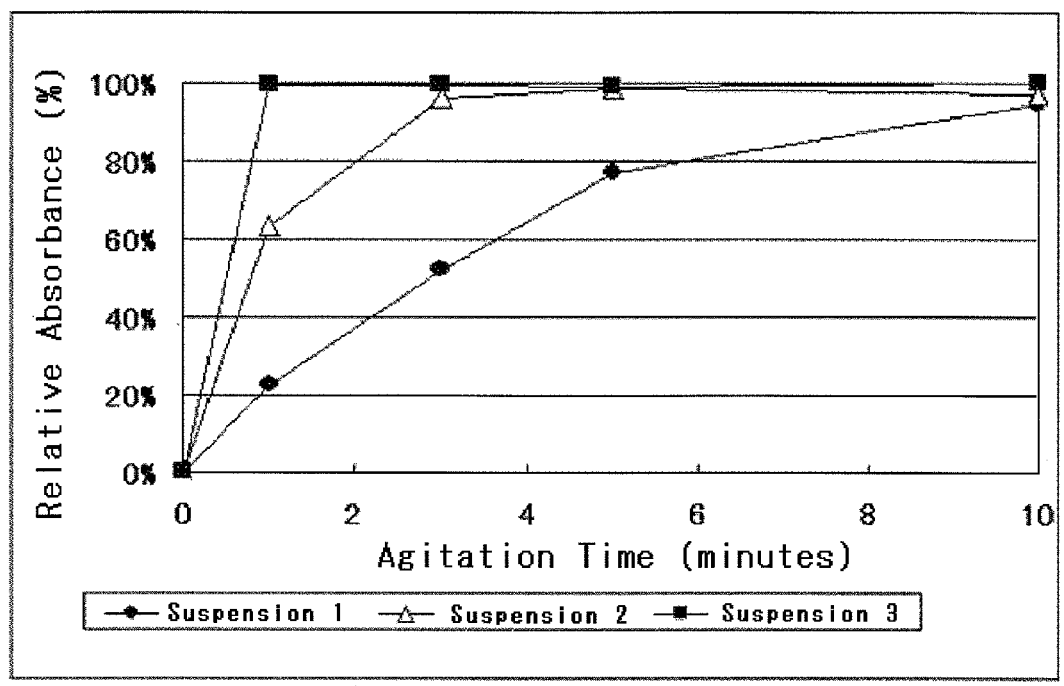
FIG. 5 is a graph showing relative absorbance percentages obtained when the dispersibility of magnetic particles in Suspensions 1 to 3 was measured.

FIG. 5 shows a plot of the relative absorbance values of Suspensions 1 to 3.
It is apparent from these results that when the silicone antifoam agent-containing suspension is used, the dispersibility of the magnetic particles is improved, and the magnetic particles can be dispersed in a short time.
It is also apparent that when the suspension used contains a silicone antifoam agent and sodium citrate, the addition of sodium citrate further improves the dispersibility of the magnetic particles.
Next, Example 2 using a polycarboxylic acid other than citric acid, specifically, potassium sodium tartrate tetrahydrate, was performed to determine whether the improvement of dispersibility by the suspension containing a silicone antifoam agent and sodium citrate is attributable specifically to citric acid or attributable to any polycarboxylic acid.

Example 2

Figure 6:
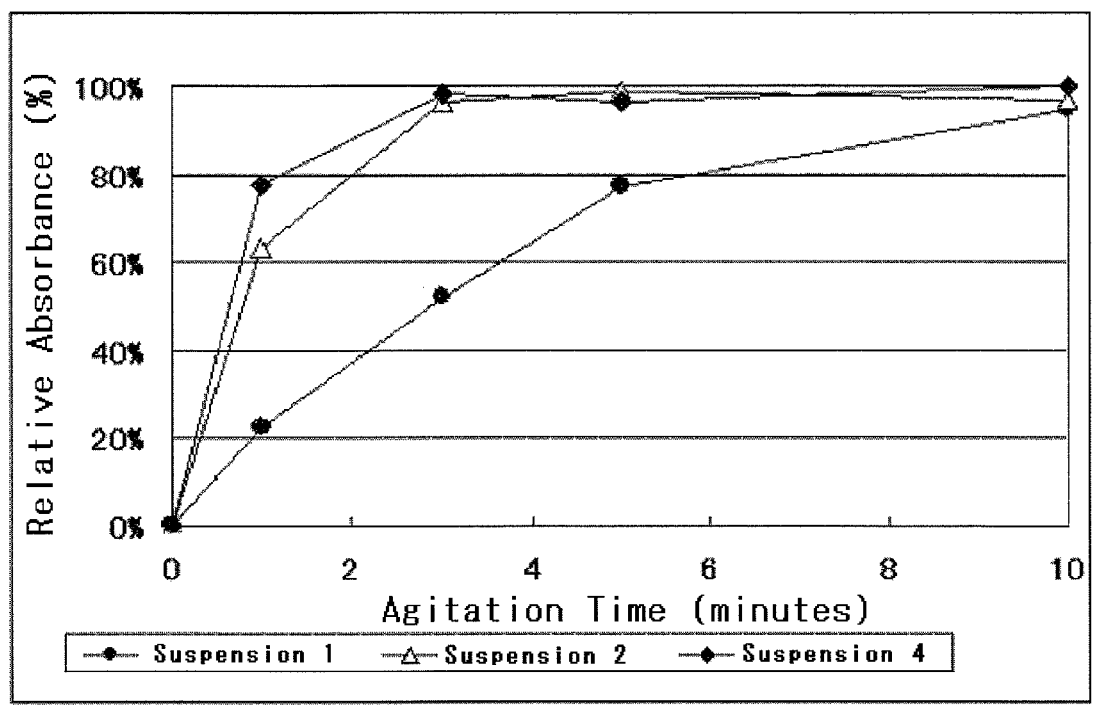
FIG. 6 is a graph showing relative absorbance percentages obtained when the dispersibility of magnetic particles in Suspensions 1, 2 and 4 was measured.

Preparation of Suspension 4
Suspension 4 was prepared as shown below.
Suspension 4
Commercial magnetic particles (2 μm in average particle size) 0.5%
MES (2-morpholonoethanesulphonic acid) (pH6.5) 20 mM
BSA 0.1%
NaN3 0.1%
Antifoam SI (Wako Pure Pure Chemical Industries, Ltd.) 0.015%
Potassium sodium tartrate tetrahydrate 10 mM
Evaluation of Particle Dispersibility
Suspension 4 and Suspensions 1 and 2 prepared in Example 1 were evaluated for dispersibility using the same particle dispersibility evaluation method as in Example 1.
FIG. 6 shows a plot of the relative absorbance values of Suspensions 1, 2 and 4.
It is apparent from these results that when the suspension used contains a silicone antifoam agent and potassium sodium tartrate tetrahydrate, the dispersibility of the magnetic particles is improved, and the magnetic particles can be dispersed in a short time.
It is also apparent that the effect of improving the dispersibility of the magnetic particles is enhanced when at least one selected from the group consisting of polycarboxylic acids such as citric acid (in the form of sodium citrate) and tartaric acid (in the form of potassium sodium tartrate tetrahydrate) is used.
Next, Example 3 using a polycarboxylic acid, specifically, sodium citrate was performed to determine whether or not the improvement of dispersibility by the suspension containing a silicone antifoam agent and a polycarboxylic acid depends on the polycarboxylic acid concentration.

Example 3

Preparation of Suspensions 5 to 7
Suspensions 5 to 7 were prepared as shown below.

Suspension 5
Commercial magnetic particles (2 μm in average particle size) 0.5%
MES (2-morpholonoethanesulphonic acid) (pH6.5) 20 mM
BSA 0.1%
NaN3 0.1%
Antifoam SI (Wako Pure Pure Chemical Industries, Ltd.) 0.015%
Sodium citrate 0.1 mM
(2) Suspension 6
Commercial magnetic particles (2 μm in average particle size) 0.5%
MES (2-morpholonoethanesulphonic acid) (pH6.5) 20 mM
BSA 0.1%
NaN3 0.1%
Antifoam SI (Wako Pure Pure Chemical Industries, Ltd.) 0.015%
Sodium citrate 1 mM
Suspension 7
Commercial magnetic particles (2 μm in average particle size) 0.5%
MES (2-morpholonoethanesulphonic acid) (pH6.5) 20 mM
BSA 0.1%
NaN3 0.1%
Antifoam SI (Wako Pure Pure Chemical Industries, Ltd.) 0.015%
Sodium citrate 1 mM Evaluation of Particle Dispersibility Suspensions 5 to 7 and Suspension 1 prepared in Example 1 were evaluated for dispersibility using the same particle dispersibility evaluation method as in Example 1.

Figure 7:
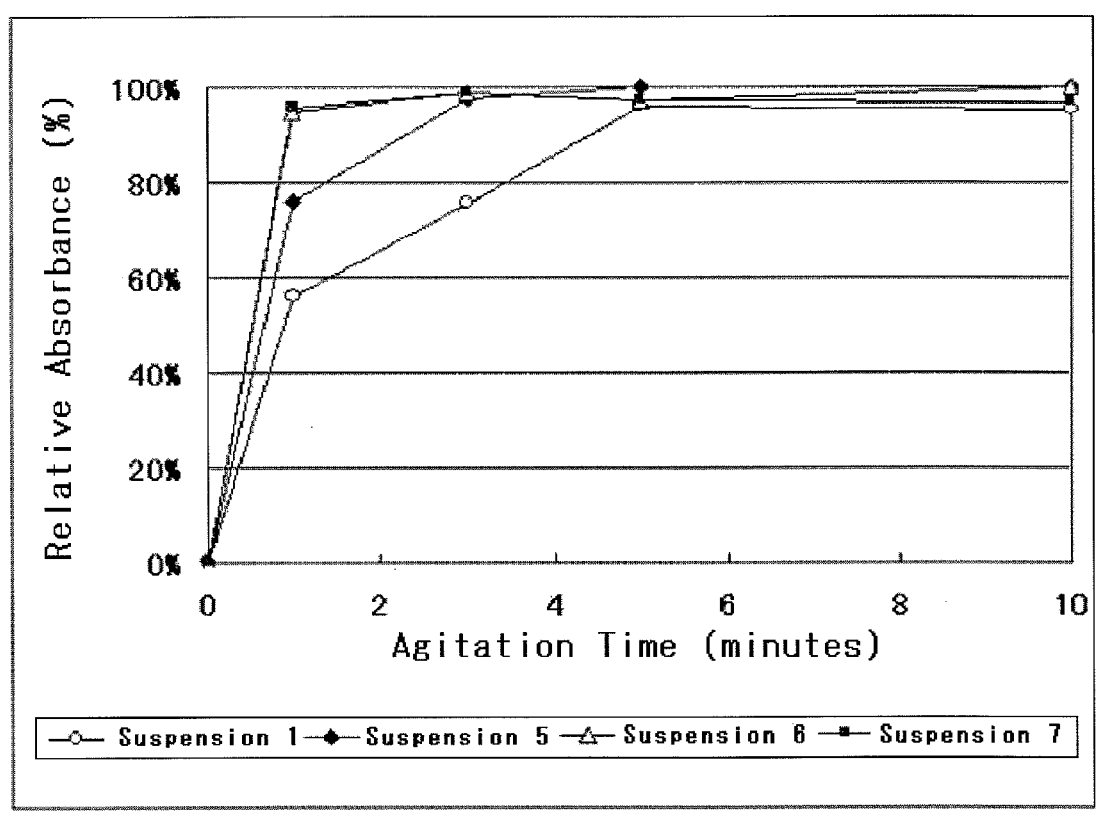
FIG. 7 is a graph showing relative absorbance percentages obtained when the dispersibility of magnetic particles in Suspensions 1 and 5 to 7 was measured.

FIG. 7 shows a plot of the relative absorbance values of Suspensions 1 and 5 to 7.

It is apparent from these results that as the concentration of sodium citrate in the suspension containing a silicone antifoam agent and sodium citrate increases, the dispersibility of the magnetic particles increases, so that the magnetic particles can be dispersed in a shorter time.

The dispersibility of the magnetic particles is higher in Suspension 7 than in Suspension 1. This indicates that the effect of further increasing the dispersibility can be obtained when the concentration of citric acid in the suspension is 0.1 mM or more.

Next, Example 4 using a polycarboxylic acid, specifically, sodium citrate, in the absence of a silicone antifoam agent was performed to determine whether or not the improvement of dispersibility by the suspension containing a silicone antifoam agent and a polycarboxylic acid is attributable only to the presence of the polycarboxylic acid.

Example 4

Preparation of Suspensions 8 to 10
Suspensions 8 to 10 were prepared as shown below.
Suspension 8
Commercial magnetic particles (2 μm in average particle size) 0.5%
MES (2-morpholonoethanesulphonic acid) (pH6.5) 20 mM
BSA 0.1%
NaN3 0.1%
Sodium citrate 0.1 mM
Suspension 9
Commercial magnetic particles (2 μm in average particle size) 0.5%
MES (2-morpholonoethanesulphonic acid) (pH6.5) 20 mM
BSA 0.1%
NaN3 0.1%
Sodium citrate 0.1 mM
Suspension 10
Commercial magnetic particles (2 μm in average particle size) 0.5%
MES (2-morpholonoethanesulphonic acid) (pH6.5) 20 mM
BSA 0.1%
NaN3 0.1%
Sodium citrate 10 mM Evaluation of Particle Dispersibility Suspensions 8 to 10 and Suspension 1 prepared in Example 1 were evaluated for dispersibility using the same particle dispersibility evaluation method as in Example 1.

Figure 8:
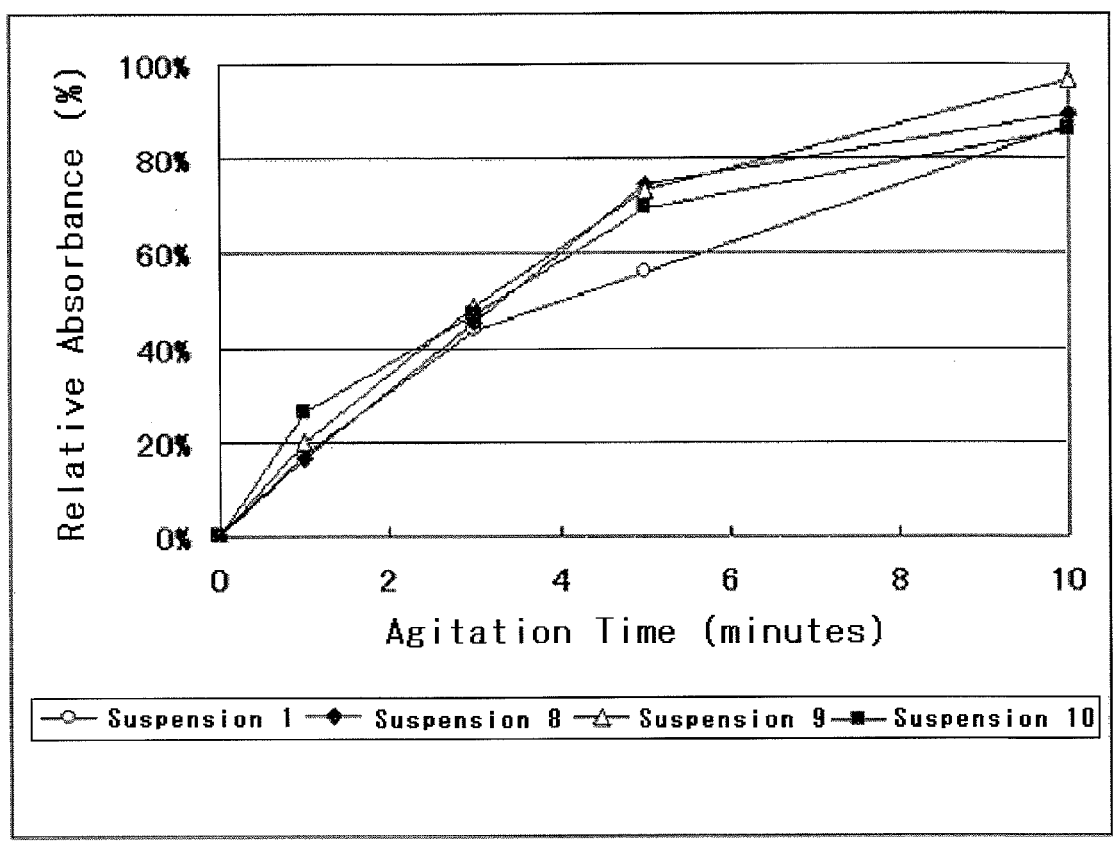
FIG. 8 is a graph showing relative absorbance percentages obtained when the dispersibility of magnetic particles in Suspensions 1 and 8 to 10 was measured.

FIG. 8 shows a plot of the relative absorbance values of Suspensions 1 and 8 to 10.

The results show that no significant improvement in the dispersibility of the magnetic particles was observed in Suspensions 8 to 10. Similarly, no significant improvement in the dispersibility of the magnetic particles was observed in Suspension 1, which contains no silicone antifoam agent or polycarboxylic acid. This indicates that the improvement in the dispersibility of magnetic particles is attributable to the presence of a silicone antifoam agent and a polycarboxylic acid and not attributable only to the presence of a polycarboxylic acid.

What is claimed is:

1. A particle suspension for use in immunoassay, comprising:
    an aqueous solvent;
    magnetic particles for use in immunoassay;
    a silicone antifoam agent; and
    polycarboxylic acid or a salt thereof,
    wherein a combination of the silicone antifoam agent and polycarboxylic acid or the salt thereof improves dispersibility of the magnetic particles in the aqueous solvent.

2. The particle suspension of claim 1, wherein the silicone antifoam agent is a silicon compound-containing antifoam agent.

3. The particle suspension of claim 2, wherein the silicon compound-containing antifoam agent is a water-soluble silicone antifoam agent.

4. The particle suspension of claim 3, wherein the water-soluble silicone antifoam agent is an emulsion type or a self-emulsifying type.

5. The particle suspension of claim 1, wherein the polycarboxylic or the salt thereof is selected from citric acid, tartaric acid, a citrate, and a tartrate.

6. The particle suspension of claim 1, wherein the polycarboxylic acid or the salt thereof is present at a concentration of 0.1 mM to 20 mM in the particle suspension.

7. A reagent kit for use in immunoassay, comprising:
    an aqueous reagent containing magnetic particles, a silicone antifoam agent, and polycarboxylic acid or a salt thereof, wherein a combination of the silicone antifoam agent and polycarboxylic acid or the salt thereof improves dispersibilty of the magnetic particles in the aqueous solvent;
    another reagent containing an antigen or antibody capable of binding to a target substance and particles; and
    a further reagent containing a labeled antigen or antibody capable of binding to the target substance.

8. The reagent kit of claim 7, wherein the silicone antifoam agent is a silicon compound-containing antifoam agent.

9. The reagent kit of claim 8, wherein the silicon compound-containing antifoam agent is a water-soluble silicone antifoam agent.

10. The reagent kit of claim 9, wherein the water-soluble silicone antifoam agent is an emulsion type or a self-emulsifying type.

11. The reagent kit of claim 7, wherein the polycarboxylic or the salt thereof is selected from citric acid, tartaric acid, a citrate, and a tartrate.

12. The reagent kit of claim 7, wherein the polycarboxylic acid or the salt thereof is present at a concentration of 0.1 mM to 20 mM in the reagent.

13. The reagent kit of claim 7, wherein the labeled antigen or antibody has an enzyme attached as a marker to it.

14. The reagent kit of claim 13, further comprising a reagent containing a substrate for reacting with the enzyme.

15. The reagent kit of claim 14, wherein the substrate is a luminescent substrate, a fluorescent substrate or a chromogenic substrate.

16. The reagent kit of claim 7, wherein the magnetic particles are not coated with antigen or antibody.

17. A particle suspension, comprising:
an aqueous solvent;
magnetic particles;
a silicone antifoam agent; and
polycarboxylic acid or a salt thereof,
wherein a combination of the silicone antifoam agent and polycarboxylic acid or the salt thereof improves dispersibility of the magnetic particles in the aqueous solvent.

* * * * *